United States Patent [19]

Thiele et al.

[11] Patent Number: 5,188,114
[45] Date of Patent: Feb. 23, 1993

[54] METHOD AND APPARATUS FOR ELIMINATION OF MIRRORING IN SIGNAL PROCESSING SYSTEM

[75] Inventors: Karl E. Thiele, Derry, N.H.; Tomohiro Hasegawa, Andover; Richard B. Smith, Tewksbury, both of Mass.

[73] Assignee: Hewlett-Packard Company, Palo Alto, Calif.

[21] Appl. No.: 606,808

[22] Filed: Oct. 31, 1990

[51] Int. Cl.$^5$ .............................................. A61B 8/06
[52] U.S. Cl. .............................. 128/661.09; 73/861.25
[58] Field of Search ............... 128/661.09; 329/311, 329/315, 320; 73/861.25; 364/413.2, 576, 724.06, 726

[56] References Cited

U.S. PATENT DOCUMENTS

| | | | |
|---|---|---|---|
| 4,607,642 | 8/1986 | Powers | 128/661.09 |
| 4,817,618 | 4/1989 | DesJardins et al. | 128/661.09 |
| 4,966,153 | 10/1990 | Nakamura et al. | 128/661.09 |
| 4,995,397 | 2/1991 | Nishiyama et al. | 128/661.09 |
| 5,048,528 | 9/1991 | Superina et al. | 128/661.09 |

Primary Examiner—Francis Jaworski

[57] ABSTRACT

In a technique for suppression of mirroring in a system which utilizes discrete Fourier transformation of an input signal, a correction apparatus adjusts the observed forward velocity spectrum by a first correction function and adjusts the observed reverse velocity spectrum by a second correction function to provide corrected velocity spectra. The first and second correction functions are representative of mismatches between the in-phase and quadrature channels of the signal processor. The correction functions are obtained during a calibration period in which calibration signals are applied to the signal processor. A first calibration signal contains frequencies of only forward velocities, and a second calibration signal contains frequencies representative of only reverse velocities. The correction functions are calculated from the spectra that were measured during calibration. In many cases, the first and second correction functions are the same.

22 Claims, 4 Drawing Sheets

METHOD AND APPARATUS FOR ELIMINATION OF MIRRORING IN SIGNAL PROCESSING SYSTEM

FIELD OF THE INVENTION

This invention relates to signal processing systems which perform a discrete complex Fourier transform of an input signal and, more particularly, to methods and apparatus for elimination of mirroring in the frequency spectra of such systems. The invention is particularly useful in medical Doppler ultrasound imaging systems, but is not limited to such use.

BACKGROUND OF THE INVENTION

Doppler ultrasound imaging systems are used to map blood flow in target regions of the human body. Ultrasonic energy is transmitted into a target region by an ultrasonic transducer. A portion of the ultrasonic energy is reflected back to the transducer. Moving cells, typically red blood cells, which have a velocity component toward or away from the transducer produce a frequency shift in the signal that is received by the transducer in accordance with the well-known Doppler principle. Red blood cells moving toward the transducer shift the ultrasound carrier higher in frequency, and cells moving away from the transducer shift the carrier lower in frequency.

The reflected signals received by the transducer are detected by a quadrature detector to provide in-phase and quadrature components of the received signal. The in-phase and quadrature signals are filtered, and a discrete Fourier transform is performed, using either digital techniques such as the fast Fourier transform or analog techniques such as the chirp-Z transform. The output of the discrete Fourier transform is a spectrum of upper sideband frequencies, or frequencies above the ultrasound carrier frequency, and a spectrum of lower sideband frequencies, or frequencies below the ultrasound carrier frequency. The Doppler equation is used to convert the sideband frequencies to velocities. The upper and lower spectra are usually nonsymmetric, since they represent forward and reverse velocities of red blood cells in the target region.

The single sideband quadrature detection technique described above uses parallel detection channels to extract the upper and lower sideband frequency information from the received signal. Each channel contains both the forward and reverse flow signals. The signals are differentiated by the phase relationships between the parallel channels.

Mirroring refers to a phenomenon in Doppler ultrasound imaging systems wherein forward flow toward the transducer appears as a reverse flow away from the transducer, and vice versa. Thus, blood flow at a particular velocity appears in the spectrum of the Doppler system as both a forward and a reverse velocity.

It is known that mirroring occurs as a result of mismatches between the in-phase and quadrature channels of the signal processing circuitry. More specifically, the quadrature detector may introduce an undesired phase shift between in-phase and quadrature signals. The filters used in the in-phase and quadrature channels may have magnitude and phase mismatches. Finally, the analog-to digital converters which digitize the in-phase and quadrature signals prior to performing the discrete Fourier transform may be mismatched. Mirroring is eliminated entirely only when the in-phase and quadrature channels are perfectly matched. The problem is complicated by the fact that the magnitude and phase of the mismatches vary with frequency so that the amount of mirroring varies as a function of frequency. In the past, mirroring has been reduced by using precision components in the in-phase and quadrature channels and/or by manually adjusting components to eliminate mismatch. However, since the magnitude and phase of the mismatch vary with frequency, mirroring may be eliminated at one velocity but may be made worse at other velocities. Furthermore, the use of precision components or manual adjustment of components adds to the cost of the system.

Signal processing circuitry which utilizes single sideband detection followed by discrete Fourier transformation is used in other applications. Examples of such applications include spectrum analyzers, network analyzers, Doppler radar systems and sonar systems. Mirroring can occur in such systems.

It is a general object of the present invention to provide improved methods and apparatus for medical Doppler ultrasound imaging.

It is another object of the present invention to provide method and apparatus for reducing or eliminating mirroring in medical Doppler ultrasound imaging systems.

It is a further object of the present invention to provide methods and apparatus for highly accurate spectral processing of signals.

It is yet another object of the present invention to provide Doppler ultrasound imaging systems which are low in cost and easy to manufacture.

It is a further object of the present invention to reduce or eliminate mirroring in signal processing circuitry which employs single sideband detection and discrete Fourier transformation.

SUMMARY OF THE INVENTION

According to the present invention, these and other objects and advantages are achieved in a method and apparatus for suppression of mirroring in a system which performs single sideband detection and discrete Fourier transformation of an input signal having a carrier frequency. The method and apparatus of the invention are particularly useful in medical Doppler ultrasound systems, but are not limited to such use. Signal processing apparatus in a Doppler ultrasound system typically includes an in-phase channel, a quadrature channel and discrete Fourier transform means for providing an observed forward velocity spectrum and an observed reverse velocity spectrum of a received ultrasound signal.

In accordance with the invention, the signal processing apparatus includes correction means for adjusting the observed forward velocity spectrum by a first correction function to provide a corrected forward velocity spectrum, and for adjusting the observed reverse velocity spectrum by a second correction function to provide a corrected reverse velocity spectrum. The first and second correction functions are representative of mismatches between the in-phase and quadrature channels and provide correction of mirroring.

The correction functions may be obtained during a calibration period prior to making a measurement with the system. The calibration includes a first calibration step in which a first calibration signal is applied to the signal processing apparatus. The first calibration signal contains one or more frequencies representative of only forward velocities. The signal processing apparatus provides a true velocity spectrum of forward velocities and a mirrored velocity spectrum of reverse velocities. The first correction function is determined as the ratio of the mirrored velocity spectrum to the true velocity spectrum.

In a second calibration step, a second calibration signal is applied to the signal processing apparatus. The second calibration signal contains one or more frequencies representative of only reverse velocities. A true velocity spectrum of reverse velocities and a mirrored velocity spectrum of forward velocities are provided by the signal processing apparatus. The second correction function is determined as the ratio of the mirrored velocity spectrum to the true velocity spectrum. In some cases, the first and second correction functions are the same, and only a single calibration step is required.

Although the in-phase and quadrature channels typically utilize local oscillator signals that are phase shifted by 90°, the correction means is capable of suppressing mirroring when the local oscillator signals have phase shifts other than 90°.

BRIEF DESCRIPTION OF THE DRAWINGS

For a better understanding of the present invention, together with other and further objects, advantages and capabilities thereof, reference is made to the accompanying drawings which are incorporated herein by reference and in which.

DETAILED DESCRIPTION OF THE INVENTION

Figure 1:
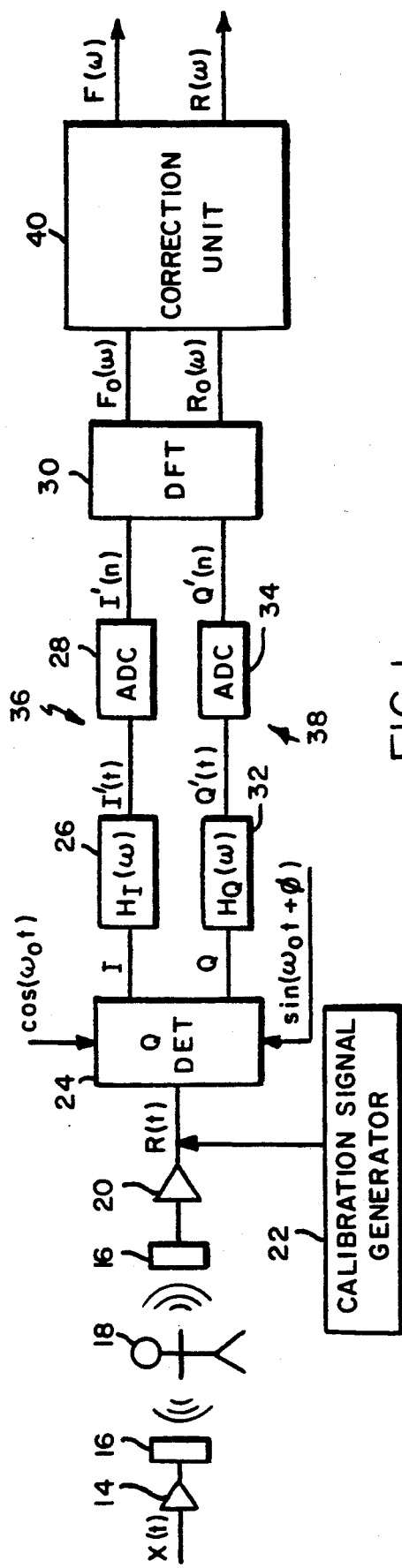
FIG. 1 is a block diagram of a Doppler ultrasound system in accordance with the present invention.

A simplified block diagram of a medical Doppler ultrasound imaging system is shown in FIG. 1. An ultrasound signal X(t), typically in the frequency range between 2 MHz and 10 MHz, is transmitted through an amplifier 14 and an ultrasonic transducer 16 into a target region of a patient 18. A portion of the transmitted ultrasonic signal is reflected from the target region of patient 18 and is received by ultrasonic transducer 16. The transducer signal is amplified by a preamplifier 20 to provide a received signal R(t). As known in the art, the frequency of the received signal is shifted to a higher frequency relative to the carrier frequency by cells, such as red blood cells, in the target region having a velocity component toward transducer 16 and is shifted to a lower frequency by cells having a velocity component away from the transducer 16. Thus, the received signal R(t) contains a spectrum of frequencies centered on the ultrasonic carrier frequency. The spectrum includes an upper frequency spectrum representative of forward velocities toward transducer 16 and a lower frequency spectrum representative of reverse velocities away from the transducer 16.

The received signal R(t) is applied to a quadrature detector 24. A calibration signal generator 22 has its output connected to the input of quadrature detector 24. The received signal R(t) is multiplied by an in-phase local oscillator signal at the carrier frequency to obtain an in-phase signal I(t), and is multiplied by a 90° phase shifted local oscillator signal at the carrier frequency to obtain a quadrature signal Q(t). The in-phase signal I(t) is applied to a series of filters 26 whose frequency response is characterized by $H_I(\omega)$. The output of the series of filters 26 is digitized by an analog-to-digital converter (ADC) 28, and is supplied to an in-phase input of a discrete Fourier transform unit 30. The quadrature signal Q(t) is supplied to a series of filters 32 whose frequency response is characterized by $H_J(\omega)$. The output of the series of filters 32 is digitized by an ADC 34 and is supplied to a quadrature input of the discrete Fourier transform unit 30. The in-phase portion of quadrature detector 24, filters 26 and ADC 28 constitute an in-phase channel 36. The quadrature portion of quadrature detector 24, filters 32 and ADC 34 constitute a quadrature channel 38.

The output of discrete Fourier transform unit 30 is an observed forward frequency spectrum $F_o(\omega)$ and an observed reverse frequency spectrum $R_o(\omega)$. As described hereinafter, the observed forward and reverse frequency spectra may include mirroring. The observed frequency spectra are supplied to the inputs of a correction unit 40 which determines a true forward frequency spectrum $F(\omega)$ and a true reverse frequency spectrum $R(\omega)$, as described in detail hereinafter.

The frequency spectrum obtained by the system of FIG. 1 is converted to a velocity spectrum according to the well known Doppler equation ($\Delta f/f_o = 2 v \cos\theta/c$, where $f_o$ is the carrier frequency of the transmitted ultrasound signal, $\Delta f$ is the frequency shift caused by movement of red blood cells in the target region, v is the velocity of the red blood cells, c is the speed of sound in tissue and $\theta$ is the angle between the velocity direction and the ultrasound beam direction). Since the relation between the frequency spectrum and the velocity spectrum is linear, the terms "frequency spectrum" and "velocity spectrum" are used interchangeably herein.

Figure 2:
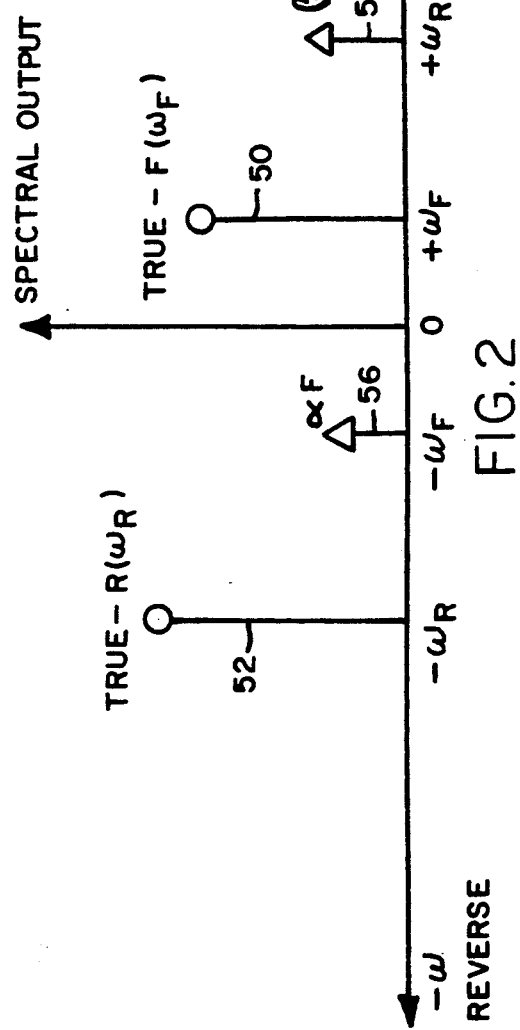
FIG. 2 is a graph of spectral output as a function of frequency, which illustrates mirroring.

An example of a spectral output of the apparatus of FIG. 1 is shown in FIG. 2. Spectral output is plotted as a function of frequency, $\omega$. Spectral outputs in the positive frequency range represent forward velocities, or velocities toward the ultrasound transducer 16. Spectral outputs in the negative frequency range represent reverse velocities, or velocities away from the ultrasound transducer 16. In the example of FIG. 1, the spectrum includes a spectral output 50 at a frequency $+\omega_F$ and a spectral output 52 at a frequency $-\omega_R$. In general, the forward and reverse spectral outputs may include multiple frequencies or a range of frequencies. The example of FIG. 2 is shown for ease of illustration. As a result of mirroring, a spectral output 54 appears at a frequency $+\omega_R$ and a spectral output 56 appears at a frequency $-\omega_F$. The spectral output 54 is caused by mirroring of spectral output 52, and the spectral output 56 is caused by mirroring of spectral output 50. The spectral outputs 54 and 56 are false indications which are caused by mismatches between the in-phase channel 36 and the quadrature channel 38.

The reason for mirroring can be determined by an analysis of the signals passing through the system of FIG. 1. The transmitted signal X(t) is given by $$X(t) = X_o \cos(\omega_o t) \quad (1)$$

where $X_o$ represents the transmitted signal amplitude and $\omega_o$ represents the carrier frequency. The received signal R(t) is given by $$R(t) = A_F \cos[(\omega_o + \omega_F)t] + A_R \cos[(\omega_o - \omega_R)t] \quad (2)$$

where $A_F$ represents the number of red blood cells moving with a forward velocity, $\omega_F$ represents the frequency shift of red blood cells moving with a forward velocity, $A_R$ represents the number of red blood cells moving with a reverse velocity and $\omega_R$ represents the frequency shift of red cells moving with a reverse velocity. The signals provided by the quadrature detector 24 include the in-phase signal I(t) and the quadrature signal Q(t). These signals are obtained by multiplying the received signal R(t) by in-phase and quadrature components of the carrier signal, respectively. The in-phase and quadrature signals are given by $$I(t) = \cos(\omega_o t) \cdot R(t) \quad 3(a)$$
$$\quad 3(b)$$
$$= A_F \cos(\omega_F t) + A_R \cos(\omega_R t) + \text{higher harmonics}$$

$$Q(t) = -\sin(\omega_o t - \phi) \cdot R(t) \quad 4(a)$$
$$\quad 4(b)$$
$$= A_F \sin(\omega_F t + \phi) - A_R \sin(\omega_R t - \phi) + \text{higher harmonics}$$

where $\phi$ represents the phase error in the quadrature detector 24. The higher harmonics are of no concern, since they can be removed by filtering. The filtered in-phase signal, I'(t) at the output of filter 26 is given by $$I'(t) = H_I(\omega_F) A_F \cos(\omega_F t) + H_I(\omega_R) A_R \cos(\omega_R t) \quad (5)$$

where $H_I(\omega)$ represents the phase and magnitude of the filter 26 response at frequency $\omega$. The filtered quadrature signal Q'(t) is given by $$Q'(t) = H_Q(\omega_F) A_F \sin(\omega_F t + \phi)$$
$$- H_Q(\omega_R) A_R \sin(\omega_R t - \phi) \quad (6)$$

where $H_Q(\omega)$ represents the phase and magnitude of the filter 32 response at frequency $\omega$. Ideally, $H_I(\omega)$ and $H_Q(\omega)$ should be matched in magnitude and phase at all frequencies. However, differences between the filter responses are one of the causes of mirroring. The relation between the filter responses can be expressed as $$H_Q(\omega) = H_I(\omega)[1 + \epsilon(\omega)] \quad (7)$$

where $\epsilon(\omega)$ represents the magnitude and phase of the mismatch between filters 26 and 32. In order to understand mirroring, it is easiest to express the filtered in-phase and quadrature signals I'(t) and Q'(t) as a complex signal S(t) as follows $$S(t) = I'(t) + j Q'(t) \quad (8)$$

where $j = \sqrt{-1}$.

By substituting equations (5), (6) and (7) into equation (8) we obtain $$S(t) = \quad (9)$$

-continued $$H_I(\omega_F) A_F \left[ \frac{1 + (1 + \epsilon(\omega_F))e^{+j\phi}}{2} \right] [\cos(\omega_F t) + j \sin(\omega_F t)] +$$

$$H_I(\omega_R) A_R \left[ \frac{1 + (1 + \epsilon(\omega_R))e^{-j\phi}}{2} \right] [\cos(\omega_R t) - j \sin(\omega_R t)] +$$

$$H_I(\omega_F) A_F \left[ \frac{1 - (1 + \epsilon(\omega_F))e^{-j\phi}}{2} \right] [\cos(\omega_F t) - j \sin(\omega_F t)] +$$

$$H_I(\omega_R) A_R \left[ \frac{1 - (1 + \epsilon(\omega_R))e^{-j\phi}}{2} \right] [\cos(\omega_R t) + j \sin(\omega_R t)]$$

The first two terms of equation (9) represent true velocities, while the last two terms of equation (9) represent mirrored velocities. Equation (9) can be simplified as follows $$S(t) = F(\omega_F)e^{+j\omega_F t} \text{ (true forward flow)} + \quad (10)$$
$$R(\omega_R)e^{-j\omega_R t} \text{ (true reverse flow)} +$$
$$\alpha(\omega_F)F(\omega_F)e^{-j\omega_F t} \text{ (mirrored forward flow)} +$$
$$\beta(\omega_R)R(\omega_F)e^{+j\omega_R t} \text{ (mirrored reverse flow)}$$

where $$F(\omega_F) = H_I(\omega_F) A_F \left[ \frac{1 + [1 + \epsilon(\omega_F)]e^{+j\phi}}{2} \right] \quad (10a)$$

$$R(\omega_R) = H_I(\omega_R) A_R \left[ \frac{1 + [1 + \epsilon(\omega_F)]e^{+j\phi}}{2} \right] \quad (10b)$$

$$\alpha(\omega_F) = \frac{1 - [1 + \epsilon(\omega_F)]e^{-j\phi}}{1 + [1 + \epsilon(\omega_F)]e^{+j\phi}} \quad (10c)$$

$$\beta(\omega_R) = \frac{1 - [1 + \epsilon(\omega_R)]e^{-j\phi}}{1 + [1 + \epsilon(\omega_F)]e^{+j\phi}} \quad (10d)$$

and $F(\omega_F)$ represents the true forward frequency spectrum, $R(\omega_R)$ represents the true reverse frequency spectrum, $\alpha(\omega_F) F(\omega_F)$ represents the mirrored forward frequency spectrum and $\beta(\omega_R) R\omega_R$ represents the mirrored reverse frequency spectrum. For the a priori assumptions specified, the $\alpha(\omega)$ and the $\beta(\omega)$ functions are the same. However, for the general case, these functions are treated as if they were not equal. Therefore, the observed forward flow $f_o(t)$ and the observed reverse flow $r_o(t)$ are as follows $$f_o(t) = F(\omega_F)e^{+j\omega_F t} + \beta(\omega_R)R(\omega_R)e^{j\omega_R t} \quad (11)$$

$$r_o(t) = R(\omega_R)e^{-j\omega_R t} + \alpha(\omega_F)F(\omega_F)e^{-j\omega_F t} \quad (12)$$

By taking the Fourier transform of the observed forward and reverse flows, we obtain $$F_o(\omega) = F(\omega_F)\delta(\omega - \omega_F) + \beta(\omega_R)R(\omega_R)\delta(\omega - \omega - \omega_R) \quad (13)$$

$$R_o(\omega) = R(\omega_R)\delta(\omega + \omega_R) + \alpha(\omega_F)F(\omega_F)\delta(\omega + \omega_F) \quad (14)$$

Where $F_o(\omega)$ represents the observed forward frequency spectrum, $R_o(\omega)$ represents the observed reverse frequency spectrum and $\delta(\omega)$ represents the impulse function. Equations (13) and (14) represent the spectral output shown in FIG. 2. The first term of equation (13) corresponds to spectral output 50, which represents a true forward velocity. The second term of equation (13) corresponds to spectral output 54, which represents a mirrored reverse velocity. The first term of equation (14) represents spectral output 52, which corresponds to a true reverse velocity, and the second term of equation (14) corresponds to spectral output 56, which represents a mirrored forward velocity.

Equations (13) and (14) can be rewritten in matrix form.

$$\begin{bmatrix} 1 & \beta(\omega) \\ \alpha(\omega) & 1 \end{bmatrix} \begin{bmatrix} F(\omega) \\ R(\omega) \end{bmatrix} = \begin{bmatrix} F_o(\omega) \\ R_o(\omega) \end{bmatrix} \quad (15)$$

Solving for the true spectra gives the following $$\begin{bmatrix} F(\omega) \\ R(\omega) \end{bmatrix} = \frac{1}{1 - \alpha(\omega)\beta(\omega)} \begin{bmatrix} 1 & -\beta(\omega) \\ -\alpha(\omega) & 1 \end{bmatrix} \begin{bmatrix} F_o(\omega) \\ R_o(\omega) \end{bmatrix} \quad (16)$$

Even for large mismatches between the in-phase and quadrature channels, the error terms $\alpha$ and $\beta$ are much smaller than 1. Therefore, the expression $1 - \alpha(\omega)\beta(\omega)$ is approximately equal to 1, and Equation (16) can be simplified as follows $$\begin{bmatrix} F(\omega) \\ R(\omega) \end{bmatrix} \approx \begin{bmatrix} 1 & \beta(\omega) \\ -\alpha(\omega) & 1 \end{bmatrix} \begin{bmatrix} F_o(\omega) \\ R_o(\omega) \end{bmatrix} \quad (17)$$

Equation (17) gives the true forward and reverse frequency spectra as a function of the observed forward and reverse frequency spectra and the mismatch terms $\alpha$ and $\beta$. Assuming that the functions $\alpha(\omega)$ and $\beta(\omega)$ have been determined, the true frequency spectra can be computed in real time by the correction unit 40 from the observed frequency spectra in accordance with Equation (17). The correction unit 40 can include an advanced digital signal processing chip such as a type TMS320XX, manufactured by Texas Instruments, for storing the values of $\alpha(\omega)$ and $\beta(\omega)$ and for performing the calculations in accordance with equation (17).

The mismatch functions $\alpha(\omega)$ and $\beta(\omega)$ are determined in a calibration procedure prior to making a measurement with the Doppler imaging system. The calibration procedure involves the application to the input of quadrature detector 24 of a calibration signal from calibration signal generator 22. The observed forward frequency spectrum $F_o(\omega)$ and the observed reverse frequency spectrum $R_o(\omega)$ at the output of discrete Fourier transform unit 30 are determined, and the functions $\alpha(\omega)$ and $\beta(\omega)$ are calculated and stored. The calibration procedure involves two steps. In the first step, the calibration signal includes only frequencies representing forward velocities. Thus, any spectral outputs in the reverse frequency spectrum must be caused by mirroring. Similarly, the second calibration step involves application of a calibration signal containing only frequencies representative of reverse velocities. Therefore, any spectral output in the forward frequency spectrum must be caused by mirroring. It will be understood that the sequence of calibration signals can be reversed if desired, or, because $\alpha(\omega)$ and $\beta(\omega)$ could be the same function, a single calibration can be performed such that $\beta(\omega)$ is assigned the $\alpha(\omega)$ values. The functions $\alpha(\omega)$ and $\beta(\omega)$ are calculated as described below from the observed frequency spectra which result from the calibration signals.

Figure 3:
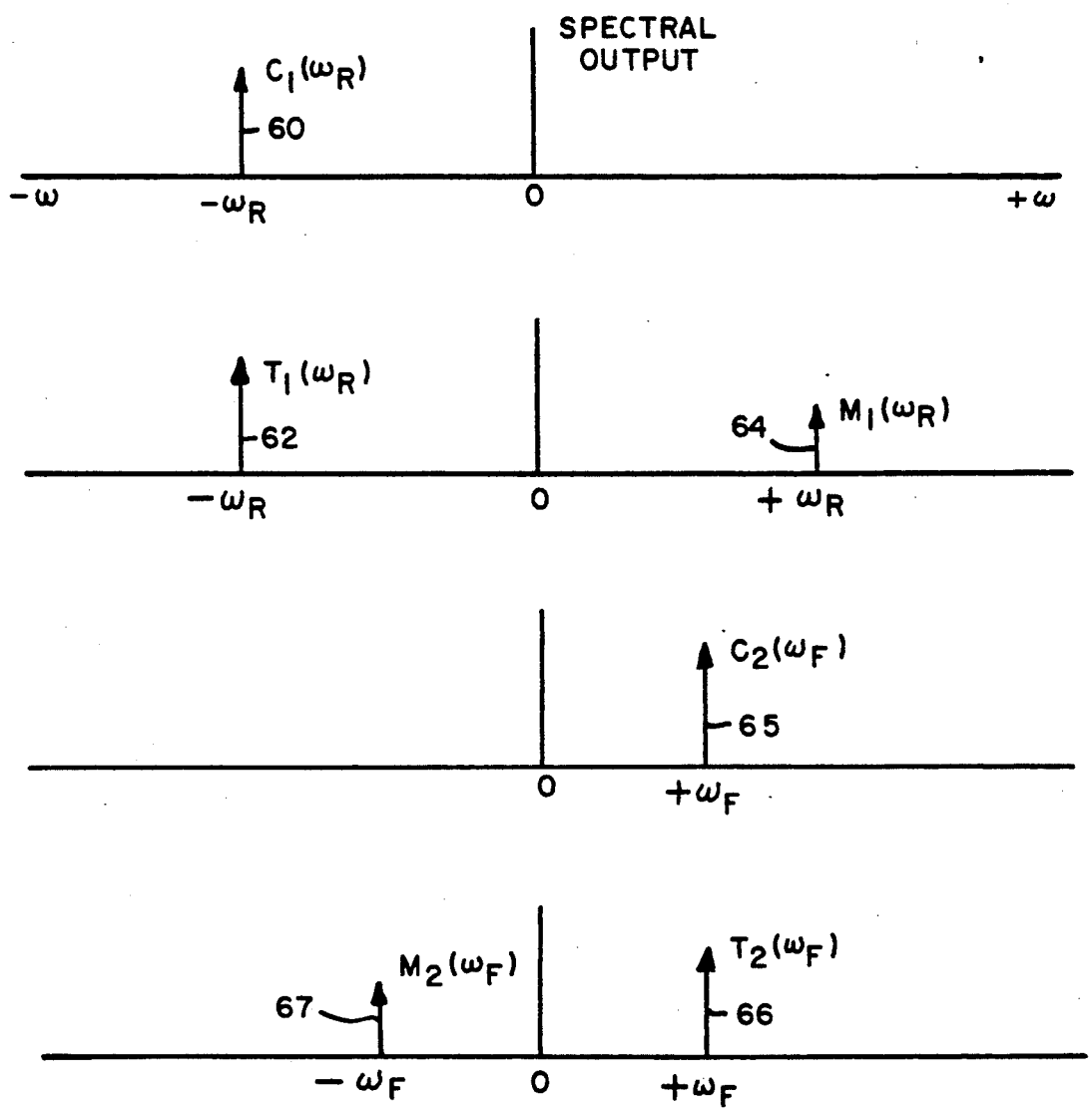
FIG. 3 shows calibration signals and corresponding observed spectra in accordance with a preferred technique for calibrating a Doppler ultrasound system.

One embodiment of the calibration procedure is illustrated in FIG. 3. The calibration signal comprises the ultrasound carrier modulated by a single tone 60 at a frequency $-\omega_R$ representative of a reverse velocity. The calibration signal, $C_1(\omega_R)$, is applied to the quadrature detector 24 by the calibration signal generator 22. The output of discrete Fourier transform unit 30 includes a true spectral output 62, $T_1(\omega_R)$, at a frequency $-\omega_R$ and a mirrored spectral output 64, $M_1(\omega_R)$, at a frequency $+\omega_R$. Since the calibration signal, $C_1(\omega_R)$, included only a single tone 60, the spectral output 64 must be a result of mirroring. The value of $\beta$ at frequency $-\omega_R$ is determined as follows $$\beta(\omega) = \frac{M_1(\omega)}{T_1(\omega)} \quad (18)$$

This procedure is repeated for a number of calibration signal tones representative of different reverse velocities, and the value of $\beta$ is determined at for each tone frequency. Then a calibration signal, $C_2(\omega_F)$, wherein a tone 65 has a frequency $+\omega_F$ representative of a forward velocity is applied to the quadrature detector 24. The output of the system is a true spectral output 66, $T_2(\omega_F)$, at a frequency $+\omega_F$ and a mirrored spectral output 67, $M_2(\omega_F)$, at a frequency $-\omega_F$. The value of $\alpha$ at frequency $+\omega_F$ is determined according to $$\alpha(\omega) = \frac{M_2(\omega)}{T_2(\omega)} \quad (19)$$

This procedure is repeated for a number of calibration signal tones representative of different forward velocities, and the value of $\alpha$ is determined for each tone frequency. The functions $\alpha(\omega)$ and $\beta(\omega)$ are stored for use in correcting the observed forward and reverse velocity spectra in accordance with Equation (17) as described above.

It will be understood that the calibration procedure described above, while effective, can be somewhat lengthy due to the requirement for sequentially taking measurements at a plurality of different tone frequencies. The Doppler imaging system may, for example, have over 100 frequency bins or resolution cells, thereby necessitating the measurement of $\alpha$ and $\beta$ at over 100 different frequencies.

Figure 4:
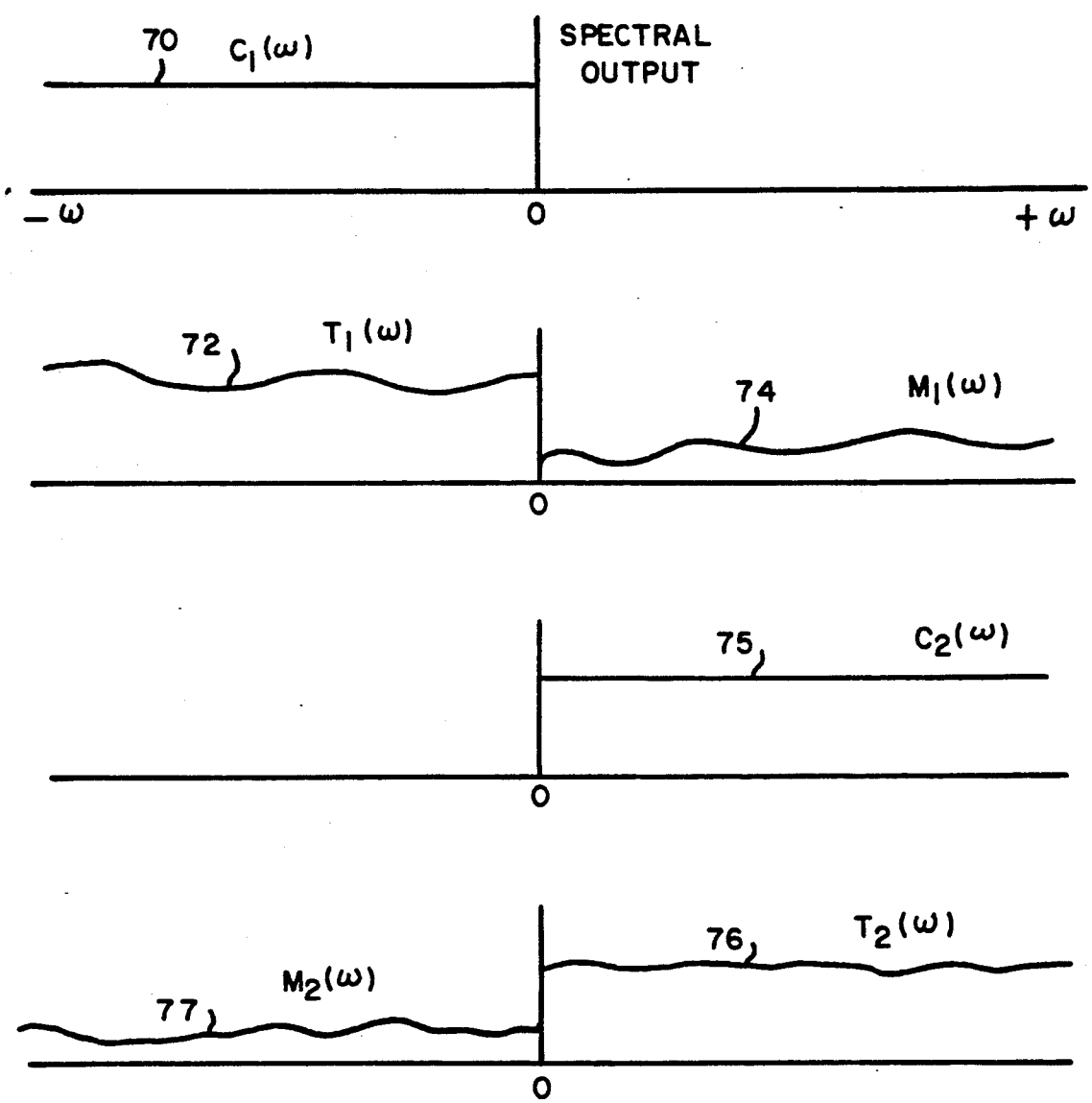
FIG. 4 shows calibration signals and observed spectra in accordance with another preferred technique for calibrating the Doppler ultrasound system.

A calibration procedure which involves only two calibration signals is illustrated in FIG. 4. A first calibration signal, $C_1(\omega)$, applied to the quadrature detector 24 by calibration signal generator 22 has a spectrum 70 that is substantially uniform over a range of frequencies corresponding to the desired range of reverse velocities. The spectral content of the calibration signal, $C_1(\omega)$, in the range representative of forward velocities is zero. The calibration signal can be a pseudo white noise signal. The output of the discrete Fourier transform unit 30 corresponding to the calibration signal having the spectrum 70 includes an observed true spectrum 72, $T_1(\omega)$, in a range of frequencies corresponding to reverse velocities and an observed mirrored spectrum 74, $M_1(\omega)$, in a range of frequencies corresponding to forward velocities. Since the calibration signal, $C_1(\omega)$, contained no frequencies corresponding to forward velocities, the mirrored spectrum 74 must result entirely from mirroring. The function of $\alpha(\omega)$ is calculated from Equation (19).

Next, a second calibration signal 75, $C_2(\omega)$, having a uniform spectral distribution in a frequency range corresponding to forward velocities is applied to quadrature detector 24. The second calibration signal 75, $C_2(\omega)$, has zero spectral content in a range of frequencies corresponding to reverse velocities. An observed true spectrum 76, $T_2(\omega)$, in the forward velocity range and an observed mirrored spectrum 77, $M_2(\omega)$, in the reverse velocity range are used to compute $\alpha(\omega)$ in accordance with Equation (19).

In accordance with this calibration procedure, the functions $\alpha(\omega)$ and $\beta(\omega)$ are obtained with only two calibration signals. Thus, calibration is completed in a much shorter time compared to the first calibration procedure described above.

After the functions $\alpha(\omega)$ and $\beta(\omega)$ have been determined, the observed forward and reverse frequency spectra can be corrected as they are determined in accordance with Equation (17), thereby providing true forward and reverse frequency spectra, $F(\omega)$ and $R(\omega)$, which are free of mirroring. The second calibration technique shown in FIG. 4 and described above requires that the discrete Fourier transform unit 30 use a rectangular window on the input data before calculating the transform.

Figure 5A:
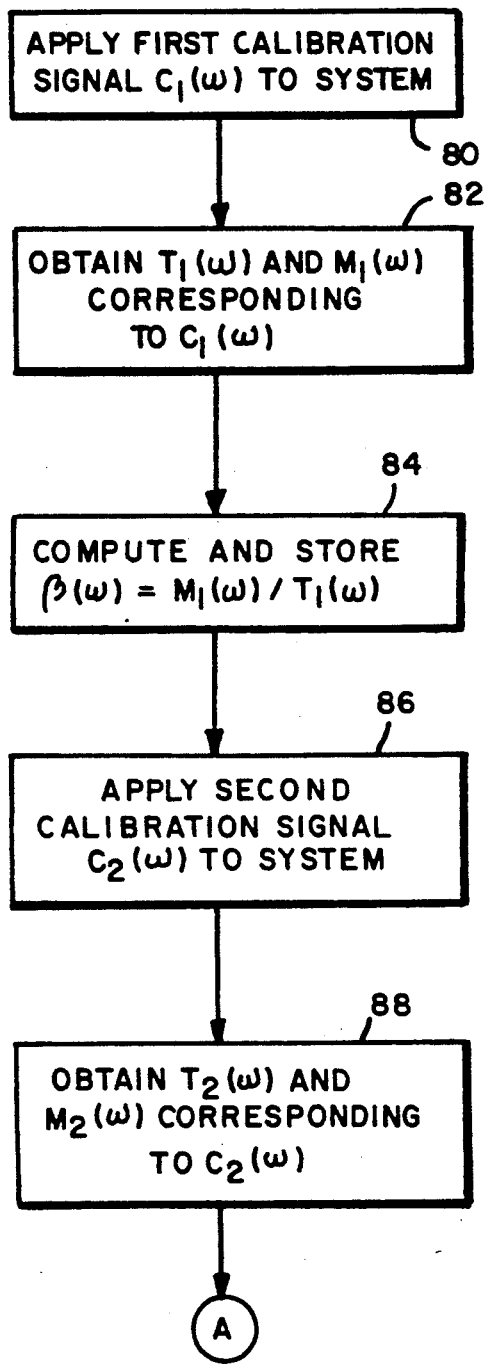
FIGS. 5A and 5B are flow diagrams, which illustrate the method for suppression of mirroring in accordance with the present invention.
Figure 5B:
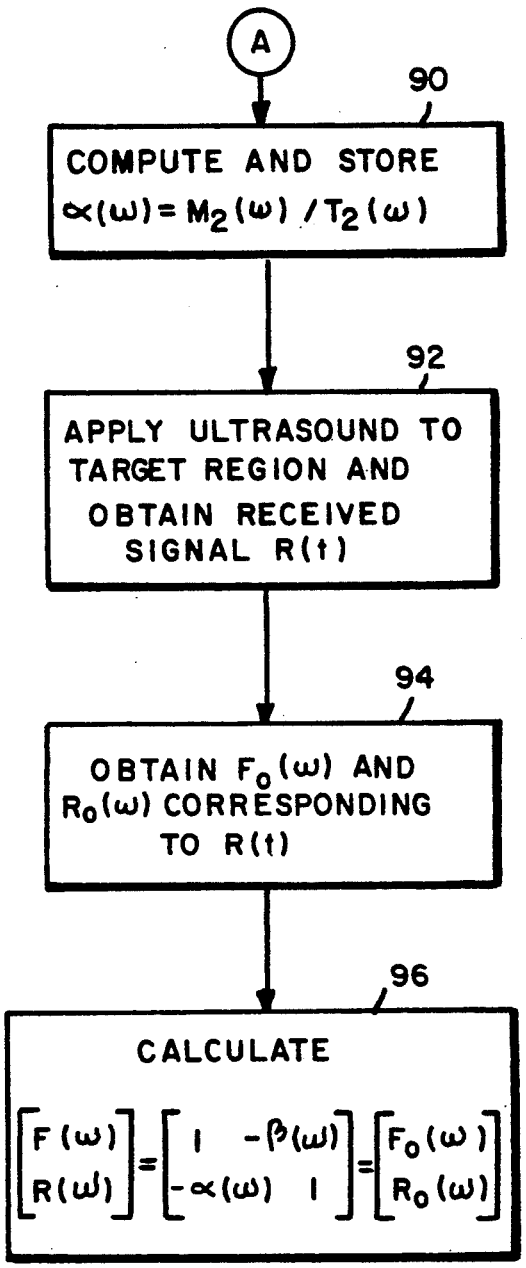

The calibration and correction technique of the present invention is summarized with reference to the flow chart of FIGS. 5A and 5B. A first calibration signal $C_1(\omega)$ is applied to the quadrature detector 24 in step 80. The calibration $C_1(\omega)$ can be one of the calibration signals described above in the alternate calibration procedures. The calibration signal $C_1(\omega)$ includes only frequencies representative of reverse velocities. The true spectrum, $T_1(\omega)$, and the mirrored spectrum, $M_1(\omega)$, corresponding to $C_1(\omega)$ are obtained in step 82. The function $\beta(\omega)$ is computed as the ratio of $M_1(\omega)$ to $T_1(\omega)$ and is stored in step 84. It will be understood that if the calibration procedure which employs single tones is utilized, then steps 80-84 must be repeated for a plurality of different tone frequencies. Next, the second calibration signal $C_2(\omega)$ is applied to quadrature detector 24 in step 86. The calibration signal $C_2(\omega)$ contains frequencies corresponding only to forward velocities. The true spectrum $T_2(\omega)$ and the mirrored spectrum $M_2(\omega)$ corresponding to $C_2(\omega)$ are determined at the output of discrete Fourier transform unit 30 in step 88. Then the function $\alpha(\omega)$ is computed as the ratio of $M_2(\omega)$ to $T_2(\omega)$ and is stored in step 90. It will be understood that steps 86, 88 and 90 can be interchanged with steps 80, 82 and 84 if desired.

After completion of step 90, the system is calibrated and is ready for normal operation. In step 92, an ultrasound signal is applied to a target region of a patient and a received signal R(t) appears at the input of quadrature detector 24. The observed forward frequency spectrum $F_o(\omega)$ and the observed reverse frequency spectrum $R_o(\omega)$ are determined by the signal processing apparatus in step 94. Then the correction unit 4 calculates the true forward frequency spectrum $F(\omega)$ and the true reverse frequency spectrum $R(\omega)$ in accordance with Equation (17) in step 96. The true frequency spectra are free of mirroring as described above.

It will be understood that the calibration procedure which determines $\alpha(\omega)$ and $\beta(\omega)$ can be performed more or less frequently, depending on the required accuracy and the operational details of the system. For example, the calibration procedure can be performed each time the system is powered up, and the same values of $\alpha$ and $\beta$ can be used thereafter. In some systems, the Doppler velocity measurement is only one of several operating modes of the system. In this case, the calibration can be repeated each time the system is switched into the Doppler mode. Such systems also typically include the capability to cover different frequency ranges. In this situation, it may be desirable to recalibrate the system each time a different frequency range selected by the user. The calibration procedure can be preprogrammed to occur automatically at the desired time, such as upon power up or when the system is switched into the Doppler mode.

The above described calibration and correction procedure is based on determination of complex values of $\alpha$ and $\beta$. Thus, a magnitude and phase is associated with $\alpha$ and $\beta$ at each different frequency. The procedure can be simplified somewhat by determining the correction values from the magnitudes of the observed spectra during calibration. Thus, the magnitudes rather than the complex values of $T(\omega)$ and $M(\omega)$ are determined at each frequency of interest. This simplifies the calculations but tends to overcompensate for mirroring somewhat. In another variation of the calibration and correction technique, $\alpha$ and $\beta$ are approximated as constants which do not vary with frequency. Although this approximation does not totally eliminate mirroring, it can sometimes reduce mirroring to an acceptable lever over a frequency range of interest.

The calculations of $\alpha$ and $\beta$ tend to become unreliable for those frequencies that correspond to the stop bands of the filters 26 and 32. The values of $\alpha$ and $\beta$ in such frequency ranges can either be ignored or weighted with a signal to-noise parameter.

The present invention has been described hereinabove in connection with a medical Doppler ultrasound imaging system. It will be understood that the problem of mirroring can arise in any signal processing system which utilizes single sideband detection followed by discrete Fourier transformation. Examples of such systems include spectrum analyzers, network analyzers, Doppler radar systems and sonar systems. The techniques described herein for reducing or eliminating mirroring can be applied to such systems.

In addition, the use in quadrature detector 24 of local oscillators that are nominally in quadrature phase relationship to each other has been assumed. The principles of the present invention can be used to correct for phases that do not have such a phase relationship. For example, two local oscillator signals having a phase relationship of $\cos(\omega_c)$ and $\cos(\omega_c + 60°)$ could be used to derive the "I" and "Q" signals. This feature may be important where it is difficult or impractical to provide local oscillator signals with a 90° phase relationship.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A medical ultrasound system comprising: transmitter means for transmitting ultrasound energy into a target region of a patient;

receiver means for receiving ultrasound energy that was transmitted into the target region of the patient by said transmitter means and providing a received signal;

an in-phase channel for extracting from the received signal an in-phase signal representative of velocities in the target region;

a quadrature channel for extracting from the received signal a quadrature signal representative of velocities in the target region;

discrete Fourier transform means for converting said in-phase signal and said quadrature signal to an observed forward velocity spectrum and an observed reverse velocity spectrum; and correction means for adjusting said observed forward velocity spectrum by a first correction function to provide a corrected forward velocity spectrum, said first correction function comprising $M_1(\omega)/T_1(\omega)$, where $M_1(\omega)$ represents a mirrored velocity spectrum and $T_1(\omega)$ represents a true velocity spectrum obtained when a first calibration signal containing one or more frequencies representative of only reverse velocities is applied to said system, and for adjusting said observed reverse velocity spectrum by a second correction function to provide a corrected reverse velocity spectrum, said second correction function comprising $M_2(\omega)/T_2(\omega)$, where $M_2(\omega)$ represents a mirrored velocity spectrum and $T_2(\omega)$ represents a true velocity spectrum obtained when a second calibration signal containing one or more frequencies representative of only forward velocities is applied to said system, said first and second correction functions being representative of mismatches between said in-phase channel and said quadrature channel.

2. A medical ultrasound system as defined in claim 1 wherein said in-phase channel includes an in-phase detector, a first filter means and a first analog-to-digital converter, and said quadrature channel includes a quadrature detector, a second filter means and a second analog-to-digital converter.

3. A medical ultrasound system as defined in claim 1 wherein said first and second correction functions have magnitudes and phases that vary with frequency.

4. A medical ultrasound system as defined in claim 1 wherein said first and second correction functions have magnitudes that vary with frequency and have constant phases.

5. A medical ultrasound system as defined in claim 1 wherein said first and second correction functions have constant magnitudes and phases as a function of frequency.

6. A medical ultrasound system as defined in claim 1 wherein said first and second correction functions are the same.

7. A medical ultrasound system as defined in claim 2 wherein said in-phase detector and said quadrature detector are driven by local oscillator signals having a phase relationship that is different from 90°.

8. In a medical Doppler ultrasound system, a method for suppression of mirroring, comprising the steps of:

performing with said system a first calibration step by applying to said system a first calibration signal $C_1(\omega)$ containing one or more frequencies representative of only reverse velocities and obtaining a true velocity spectrum $T_1(\omega)$ and a mirrored velocity spectrum $M_1(\omega)$;

performing with said system a second calibration step by applying to said system a second calibration signal $C_2(\omega)$ containing one or more frequencies representative of only forward velocities and obtaining a mirrored velocity spectrum $M_2(\omega)$ and a true velocity spectrum $T_2(\omega)$;

determining with said system a first correction function from the spectra obtained in said first calibration step and a second correction function from the spectra obtained in said second calibration step;

performing with said system a Doppler ultrasound measurement of a target region of a patient and obtaining an observed forward velocity spectrum and an observed reverse velocity spectrum; and correcting said observed forward velocity spectrum with said first correction function to obtain a corrected forward velocity spectrum and correcting said observed reverse velocity spectrum with said second correction function to obtain a corrected reverse velocity spectrum.

9. A method for suppression of mirroring as defined in claim 8 wherein said first calibration signal has a substantially flat frequency spectrum over a range of frequencies corresponding to reverse velocities of interest and zero spectral content over a frequency range corresponding to forward velocities of interest.

10. A method for suppression of mirroring as defined in claim 8 wherein said second calibration signal has a substantially flat frequency spectrum over a range of frequencies corresponding to forward velocities of interest and a zero spectral content over a range of frequencies corresponding to reverse velocities of interest.

11. A method for suppression of mirroring as defined in claim 8 wherein the step of determining a first correction function includes determining the ratio $M_1(\omega)/T_1(\omega)$.

12. A method for suppression of mirroring as defined in claim 8 wherein the step of determining a second correction function includes the step of determining the ratio $M_2(\omega)/T_2(\omega)$.

13. Apparatus for determining the spectrum of an input signal having a carrier frequency, comprising:

an in-phase channel for extracting from the input signal an in-phase signal that is in phase with the carrier frequency;

a quadrature channel for extracting from the input signal a quadrature signal that is in quadrature with the carrier frequency;

discrete Fourier transform means for converting said in-phase signal and said quadrature signal to an observed upper frequency spectrum and an observed lower frequency spectrum; and correction means for correcting said observed upper frequency spectrum with a first correction function to provide a corrected upper frequency spectrum, said first correction function comprising $M_1(\omega)/T_1(\omega)$, where $M_1(\omega)$ represents a mirrored frequency spectrum and $T_1(\omega)$ represents a true frequency spectrum obtained when a first calibration signal containing one or more frequencies higher than the carrier frequency is applied to said system, and for correcting said observed lower frequency spectrum with a second correction function to provide a corrected lower frequency spectrum, said second correction function comprising $M_2(\omega)/T_2(\omega)$, where $M_2(\omega)$ represents a mirrored frequency spectrum and $T_2(\omega)$ represents a true frequency spectrum obtained when a second calibration signal containing one or more frequencies lower than the carrier frequency is applied to said system, said first and second correction functions being representative of mismatches between said in-phase channel and said quadrature channel.

14. Apparatus as defined in claim 13 wherein said in-phase and quadrature channels are driven by local oscillator signals having a 90° phase relationship.

15. Apparatus as defined in claim 13 wherein said in-phase and quadrature channels are driven by local oscillator signals having a phase relationship that is different from 90°.

16. Apparatus as defined in claim 13 wherein said first and second correction functions are the same.

17. In apparatus which performs single sideband detection and discrete Fourier transformation of an input signal having a carrier frequency, a method for suppression of mirroring, comprising the steps of:
    performing with said apparatus a first calibration step by applying to said apparatus a first calibration signal containing one or more frequencies higher than the carrier frequency and obtaining from said apparatus upper and lower frequency spectra;
    performing with said apparatus a second calibration step by applying to said apparatus a second calibration signal containing one or more frequencies lower than the carrier frequency and obtaining from said apparatus upper and lower frequency spectra;
    determining with said apparatus a first correction function from the spectra obtained in said first calibration step and a second correction function from the spectra obtained in said second calibration step;
    obtaining with said apparatus an observed upper frequency spectrum and an observed lower frequency spectrum of an input signal; and
    correcting said observed upper frequency spectrum with said first correction function to obtain a corrected upper frequency spectrum and correcting said observed lower frequency spectrum with said second correction function to obtain a corrected lower frequency spectrum.

18. In a medical Doppler ultrasound system, a method for suppression of mirroring, comprising the steps of:
    performing with said system a calibration by applying to said system a calibration signal $C(\omega)$ containing one or more frequencies representative of only reverse velocities or only forward velocities and obtaining a true velocity spectrum $T(\omega)$ and a mirrored velocity spectrum $M(\omega)$;
    determining with said system a correction function from the spectra obtained in said calibration;
    performing with said system a Doppler ultrasound measurement of a target region of a patient and obtaining an observed forward velocity spectrum and an observed reverse velocity spectrum; and
    correcting said observed forward velocity spectrum with said correction function to obtain a corrected forward velocity spectrum and correcting said observed reverse velocity spectrum with said correction function to obtain a corrected reverse velocity spectrum.

19. A method for suppression of mirroring as defined in claim 18 wherein said calibration signal has a substantially flat frequency spectrum over a range of frequencies corresponding to reverse velocities or forward velocities of interest.

20. A method for suppression of mirroring as defined in claim 18 wherein the step of determining a correction function includes determining the ratio $M(\omega)/T(\omega)$.

21. Apparatus for determining the spectrum of an input signal having a carrier frequency, comprising:
    a first channel for extracting from the input signal a first signal that is in phase with the carrier frequency;
    a second channel for extracting from the input signal a second signal that has a predetermined phase relationship to the carrier frequency;
    discrete Fourier transform means for converting said first and second signals to an observed upper frequency spectrum and an observed lower frequency spectrum; and
    correction means for correcting said observed upper frequency spectrum with a correction function to provide a corrected upper frequency spectrum and for correcting said observed lower frequency spectrum with said correction function to provide a corrected lower frequency spectrum, said correction function comprising $M(\omega)/T(\omega)$, where $M(\omega)$ represents a mirrored frequency spectrum and $T(\omega)$ represents a true frequency spectrum obtained when a calibration signal containing one or more frequencies either higher or lower in frequency than the carrier frequency is applied to said apparatus, said correction function being representative of mismatches between said first and second channels.

22. In apparatus which performs single sideband detection and discrete Fourier transformation of an input signal having a carrier frequency, a method for suppression of mirroring, comprising the steps of:
    performing with said apparatus a calibration step by applying to said apparatus a calibration signal containing one or more frequencies either higher or lower in frequency than the carrier frequency and obtaining from said apparatus upper and lower frequency spectra;
    determining with said apparatus a correction function from the spectra obtained in said calibration step;
    obtaining with said apparatus an observed upper frequency spectrum and an observed lower frequency spectrum of an input signal; and
    correcting said observed upper frequency spectrum with said correction function to obtain a corrected upper frequency spectrum and correcting said observed lower frequency spectrum with said correction function to obtain a corrected lower frequency spectrum.

* * * * *